United States Patent [19]

Bischkopf et al.

[11] Patent Number: 4,790,662
[45] Date of Patent: Dec. 13, 1988

[54] METHOD AND DEVICE FOR INSPECTING EMPTY BOTTLES

[75] Inventors: Reiner Bischkopf, Neutraubling; Karl Griesbeck, Regensburg, both of Fed. Rep. of Germany

[73] Assignee: Krones AG Hermann Kronseder Maschinenfabrik, Neutraubling, Fed. Rep. of Germany

[21] Appl. No.: 67,610

[22] Filed: Jun. 26, 1987

[30] Foreign Application Priority Data

Jul. 1, 1986 [DE] Fed. Rep. of Germany ....... 3621976

[51] Int. Cl.$^4$ ............................................. G01N 21/90
[52] U.S. Cl. ................................ 356/428; 250/223 B; 356/240
[58] Field of Search .............................. 356/428, 240; 250/223 B

[56] References Cited

U.S. PATENT DOCUMENTS

| | | | |
|---|---|---|---|
| 3,411,009 | 11/1968 | Ford et al. ..................... | 356/428 X |
| 3,631,255 | 12/1971 | Gender .......................... | 356/240 X |
| 3,923,158 | 12/1975 | Fornaa ........................... | 250/223 B X |
| 4,063,823 | 12/1977 | Graj .............................. | 250/223 B X |

FOREIGN PATENT DOCUMENTS

| | | |
|---|---|---|
| 1432340 | 9/1964 | Fed. Rep. of Germany . |
| 1573687 | 3/1965 | Fed. Rep. of Germany . |
| 1648640 | 9/1967 | Fed. Rep. of Germany . |
| 2240833 | 8/1972 | Fed. Rep. of Germany . |
| 2262556 | 12/1972 | Fed. Rep. of Germany . |

Primary Examiner—Davis L. Willis
Assistant Examiner—Matthew W. Koren
Attorney, Agent, or Firm—Fuller, Puerner & Hohenfeldt

[57] ABSTRACT

Empty bottles are checked for foreign bodies and other contamination by passing the bottles successively through two inspection zones in which they are opto-electronically scanned while they are on rotating disks that are mounted on a rotating table. When in one inspection zone a bottle is held stable on the disk by a rotatable socket that grips the bottle mouth to allow a clear view for inspecting down to the bottom. When in the other inspection zone the bottle is engaged by a ring at about shoulder height so there is a clear view for inspection of the bottle portion from the shoulder to the mouth. In transition regions between inspection zones the ring and socket both engage the bottle for a moment and then one gripper is withdrawn while the other remains to hold the bottle in the forthcoming inspection zone.

10 Claims, 8 Drawing Sheets

METHOD AND DEVICE FOR INSPECTING EMPTY BOTTLES

BACKGROUND OF THE INVENTION

This invention pertains to a method and apparatus for inspecting empty bottles for foreign bodies, dirt spots and other contaminants.

In one known bottle inspecting apparatus, the bottles are transported along a circular path on rotating support plates which pass the bottles through an inspection zone. A gripping element grips the bottle to be inspected between the head and mouth and maintains the grip at the one place from entry to exit of the inspection zone. The bottles are also stabilized by a downwardly moving socket during passage through the inspection zone. The bottles are scanned with optoelectronics devices in an inspection zone. As a result of accurate and stable fixation of the bottles due to grasping, this known apparatus permits high transport capacities and a high degree of inspection accuracy. It is, however, disadvantageous that the uppermost region of the bottles, that is, the part of the head of the bottle immediately below the upper grasping point is not accessed well as a result of the gripping device shadowing at least a small zone on the bottle. Because users now demand that the entire lateral wall from the bottom to the mouth of a bottle be inspected thoroughly, apparatus of this kind can no longer be used. An example of such apparatus is shown in U.S. Pat. No. 3,411,009.

Another German Patent DE-AS No. 22 62 556 discloses a method for inspecting filled ampules for contamination. According to this prior method, the ampules are again grasped only once during the entire inspection process between the bottom and the shoulder and they are then moved through the inspection area along a circular path while they are being rotated by means of rotating the disks on which they are supported. This apparatus also permits high speed inspection as a result of grasping the ampules axially. Inspection, however, is limited to the relatively short vertical region of the ampules between the two grasping points while the total neck and head region which is concealed by a tube-like grasping element is not checked. This method is, therefore, also not acceptable for total lateral wall inspection.

According to another known apparatus, the bottles are pressed by fingers against rotating friction rollers which contact the wall of the bottle as it is transported through the inspection zone along a circular path. This device is disclosed in German Patent DE-AS No. 1,648,640. In this device there is no support for grasping the bottles in an axial direction. The device is suitable for inspecting the entire side wall of a bottle but it has been shown that supporting the bottles by means of lateral friction forces alone permits neither high output nor reliable testing because of deviations in form and dimensions within a category of bottles as is typical for beverage bottles.

In another known method for testing filled ampules for contamination, the ampules are grasped only in the bottom region by turntables which are equipped with a suction orifice. This device is described in German Patent DE-AS No. 1,573,687. The turntables do not have any transport function. Holding the ampules by means of vacuum after their bottom surface is practical only for relatively small and light ampules but it is not practical for large and heavy beverage bottles. With this device fixation of bottles would not be reliable enough to permit high transport speed at high quantity output of the bottles because of the tenuous grip on the bottles which vacuum provides. Irregularities in the bottom area of the bottles further weakens the vacuum grip.

Another method for detecting contaminants in empty beverage bottles is described in German Patent DE-AS No. 22 40 833. With this method the bottles are carried on a supporting surface interfaced only with their bottoms and they are moved through the inspection zone with no additional support. Checking the entire lateral wall of the bottles is easily achieved. But the stability of the free standing bottles is minimal and is not suited for high output of inspected bottles.

SUMMARY OF THE INVENTION

The invention features permitting inspecting the entire wall of a bottle from the bottom to its mouth while always maintaining the bottle in a stable and exact fixation.

According to the invention, every bottle is grasped alternately at two different places in succession as it passes through successive inspection zones. One of the inspection zones inspects the bottle from its bottom up through its shoulder region and slightly beyond while the bottle is being held or stabilized only by gripping its mouth. At the transition of the bottle from the first to the next inspection zone, the gripping device on the mouth is retracted and a ring gripping device is brought down on the shoulder of the bottle and held there through the second consecutive inspection zone. Thus, optoinspection of the entire lateral wall including the area of the mouth and the sealing surface is possible although in two separate steps. Consequently, the bottles are firmly grasped in an axial direction at all times so that extremely rapid transport and rotation speeds are possible. Because of the way the two gripping devices are handled and because of the scanning ranges in both inspection zones, there is a partial overlap of the two zones which guarantees that no zone from the bottom to the mouth of the bottle will be missed.

A more detailed description of an embodiment of the invention and the method of carrying it out will now be set forth in reference to the drawings.

DESCRIPTION OF A PREFERRED EMBODIMENT

Figure 1:
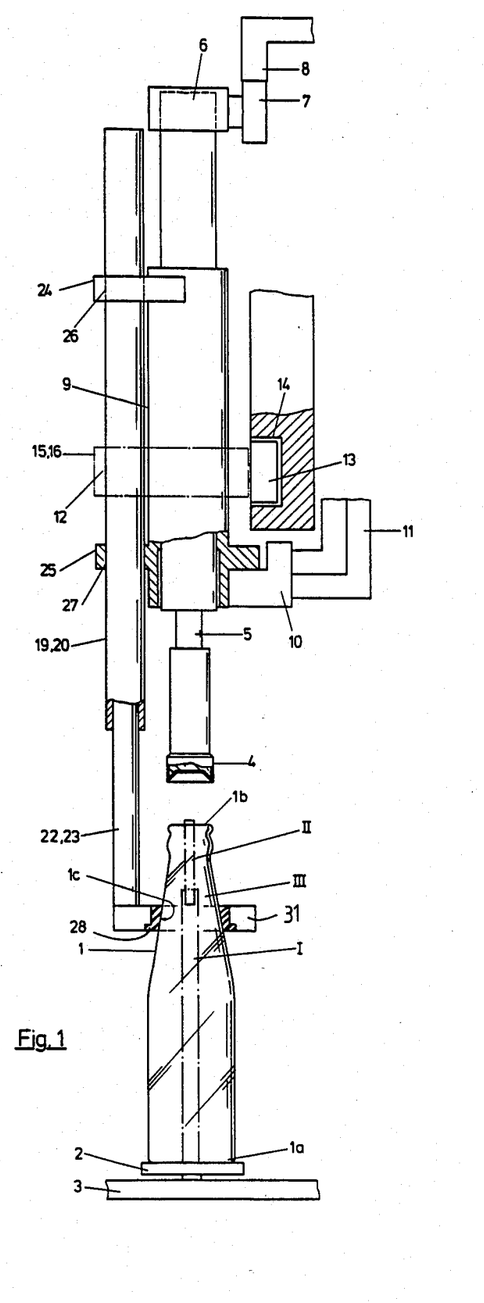
FIG. 1 is a side elevational view of the mechanism for engaging a bottle with a centering socket as the bottle is being transported through one inspection zone and for engaging the bottle in a region of its shoulder while it is being transported through another inspection zone.

In FIG. 1, a bottle 1 that is to be inspected ( is supported on one of the rotating disks 2 that are appropriately circumferentially spaced on a rotatable bottle table 3. The vertical axis of a bottle is presently aligned with a centering socket member 4 that is movable downwardly to engage the bottle at its mouth 1b to stabilize the bottle. The centering socket member is rotatable about a vertical axis. The socket member comprises a movable driving member 5 which is constantly biased in one direction by a spring that is not visible There is a guide or cam follower roller 7 at the upper end of the lifting mechanism. Rotatable roller 7 is mounted to an adapter 6. Roller 7 follows the path of a cam 8 which is fixed and is so configured that it acts on roller 7 to reciprocate at appropriate times for lowering centering socket 4 into a position for grasping the mouth 1b of the bottle and releasing the bottle 1 at an appropriate time. Driving member 5 is guided inside of an approximately cylindrical bearing block 9 which has a flange 25 for supporting the block on the boss 10 of a carousel unit 11 which is illustrated in part in FIG. 1.

Figure 2:
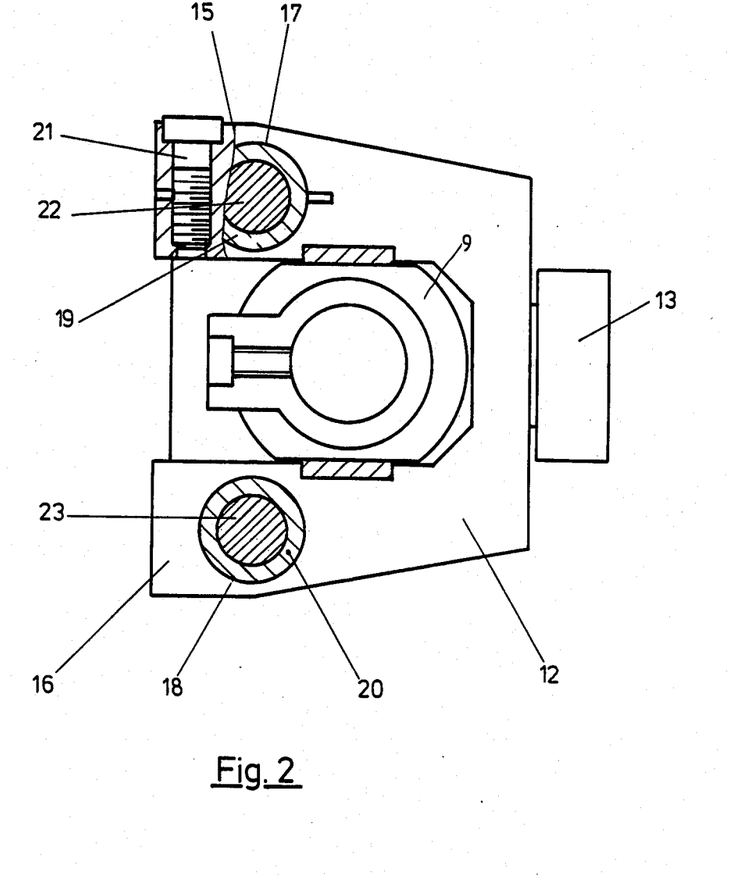
FIG. 2 is a plan view of a bifurcated sliding head with holding rods or rails.
Figure 4:
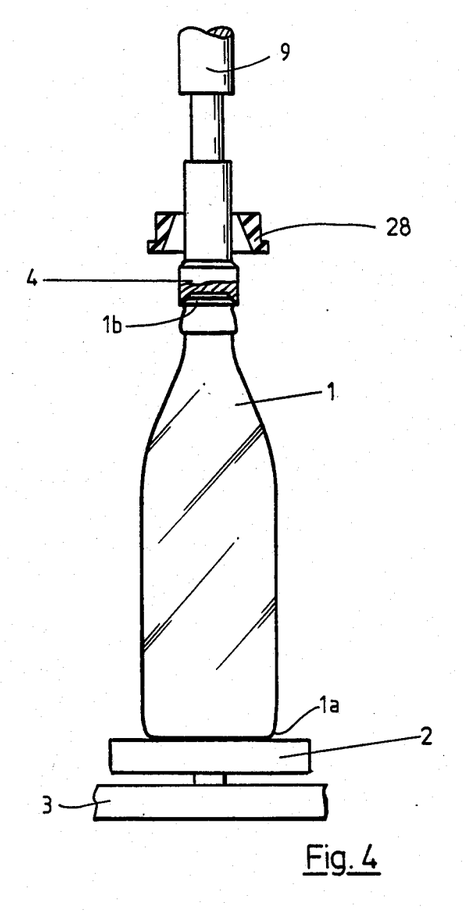
FIGS. 4–7 are schematic views showing the functioning of the grasping members in relation to the optoelectronics scanning phases.

Cylindrical bearing block 9 forms the mounting and guide element for a radially displaced bifurcated element or fork 12 which is shown in phantom in FIG. 1 and more realistically in FIG. 2. Fork 12 has a driving cam follower roller 13 mounted to it. The follower roller is reciprocated vertically by virtue of it following along an appropriately configured stationary cam groove 14 which is formed as a closed circle. FIG. 4 shows the fork to have arms 15 and 16 in which there are bore holes 17 and 18 arranged for receiving guide bushings or linear bearings 19 and 20 which are secured by clamping set screws such as the one marked 21.

Referring to FIG. 1 again, the cylindrical bearing block 9 has two transverse elements 24 and 25 attached at its upper and lower end regions, respectively. Elements or cross bars 24 and 25 have aligned bores 26 and 27 for receiving each of the bushings 19 and 20 to form a slidable support Bushings 19 and 20 are occupied by spring loaded rails or rods 22 and 23. At the lower end of rods 22 and 23 there is a centering member 31 containing a centering ring 28 which is shown diagrammatically in FIG. 1 and in greater detail in FIG. 3. Centering ring 28 reciprocates with member 31 alternately and in timed relationship with the vertical movements of fork 12. Thus, the action of cam follower roller 13 on cam 14 at certain orbital positions of the bottle and holding devices drives the centering ring 28 downward so it grasps the neck region of the bottle above the shoulder region I of the bottle 1 at which time only the centering ring 28 is actively supporting the bottle. When the centering ring 28 is holding the bottle, regions above and below it are clear and free of interference so that optoelectronic inspection of those regions can be conducted. As the bottle and its holding devices orbit further and out of the region where at least the upper portion of the bottle is scanned optoelectronically for contaminants, the holding ring 28 is retracted upwardly and at a transition point centering socket 4 is lowered to engage the bottle at its mouth and leave the rest of the bottle clear for inspection in another zone of the machine as will be explained. As has been mentioned, it is when cam follower roller 7 reaches a certain point along the stationary cam 8 that the centering socket 4 is driven down. After it has passed through the inspection zone for the body of the bottle, the centering socket 4 and centering ring 28 are both retracted to permit discharge of the bottle from the inspection machine. Note that the centering ring 28 has greater vertical movement than the centering socket and that this is accounted for by having the inner diameter of the centering ring greater than the outer diameter of the centering socket 4.

Figure 3:
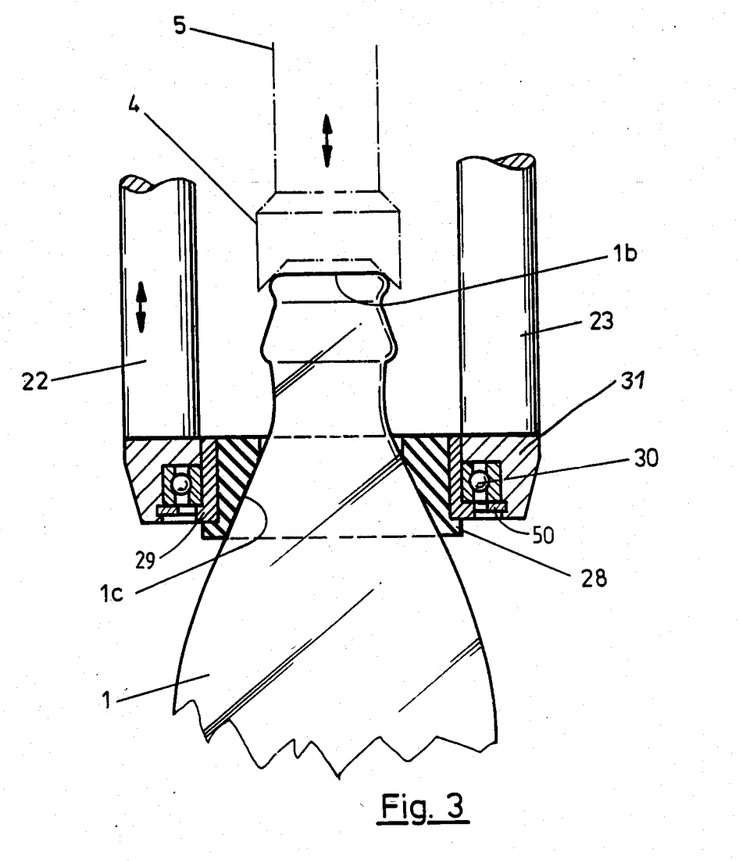
FIG. 3 shows the details of the structure for holding the bottle in a region of its shoulder and permitting the bottle to rotate about its axis as it is being transported through one of the inspection zones.

Observe in FIG. 3 that the centering ring 28 is a soft high friction material such as rubber. The rubber ring is bonded in a sleeve 29 which has a shoulder extending under a ball bearing assembly 30. The bearing is retained by a split snap ring 50 which fits into an annular groove in an element 31 which, in turn, is mounted to vertically reciprocating rods 22 and 23.

Figure 5:
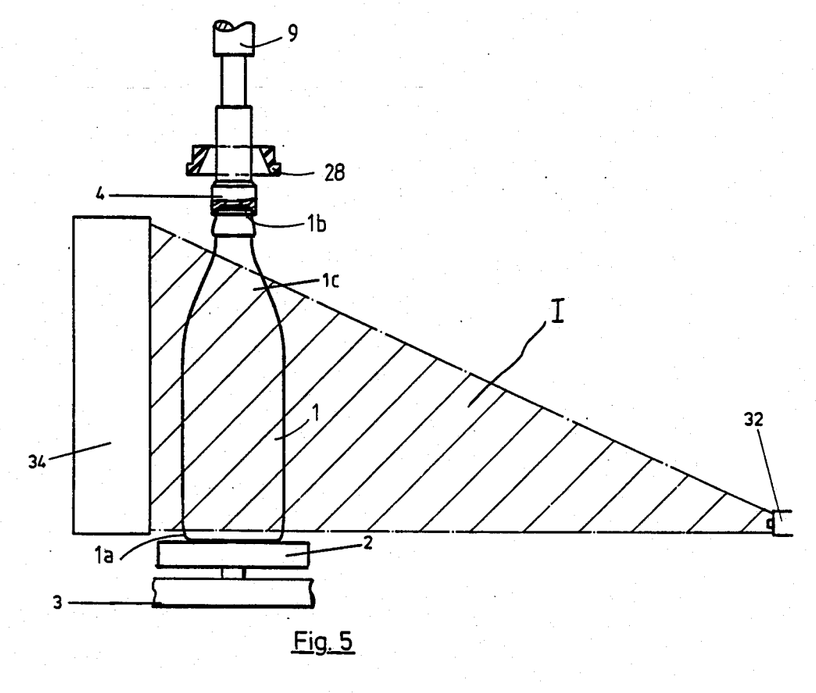
Figure 6:
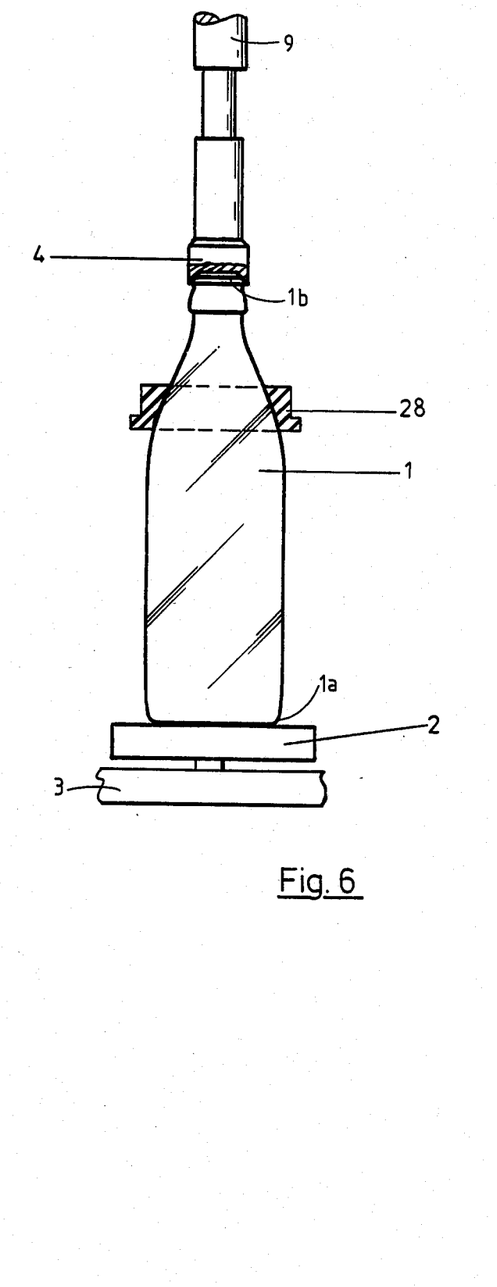
Figure 7:
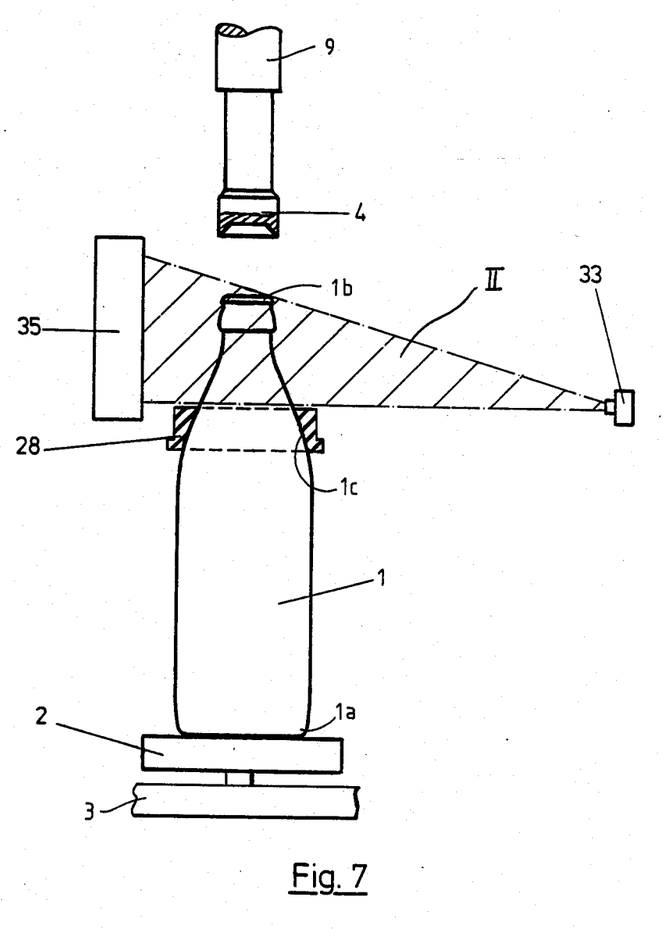

FIG. 4 shows a bottle ready to enter inspection zone I as depicted in FIG. 5. Centering ring 28 is retracted upwardly clear of the bottle 1. The bottle is rotating on disk 2 and is being transported in a circular path on rotating bottle table 3. At this time the bottle is grasped and stabilized between its bottom 1a and its mouth 1b as a result of the bottle being gripped by rotatable centering socket 4. At a transition point at the end of inspection zone I, centering ring 28 is lowered and centering socket 4 remains engaged with the mouth of the bottle for a moment as depicted in FIG. 6. Following the transition point, centering socket 4 is driven upwardly and centering ring 28 remains engaged with the bottle to stabilize it on rotating disk 2 as it enters inspection zone II as depicted in FIG. 7. At this time it is only the region 1c or shoulder of the bottle where there is interference by a holding element but the space between the bottle bottom 1a and shoulder 1c and the space above centering ring 28 and mouth 1a are clear. Since most of the bottle between its bottom 1a and its shoulder 1c has been inspected in inspection zone I as shown in FIG. 5 it is satisfactory that the part above centering ring 28 in FIG. 7 is clear of obstructions to permit inspection in zone II of part of the bottle neck that has not been completely inspected and the mouth region of the bottle as in FIG. 7. FIG. 1 shows the region III between mouth 1b and shoulder 1c of the bottle where the two inspections overlap. The machine is properly adjusted when each region of the bottle wall is scanned optoelectronically. Only one holding rod 22 or 23 would be used if it were guided well enough. The arrangement of the parts is such that holding rods 22 and 23 do not interfere with passage of the inspection light beams at all times. Rods 22 and 23 are parallel to the axis of the bottle such that when viewed in the direction of translation of the bottle the rods reside in front of the bottle or behind it so the testing light beam can pass unhindered through the top region of the bottle transversely to the direction of translation when the bottle is in an inspection zone and is being gripped by the centering ring.

It should be evident that the inspection sequence can be reversed, that is, the bottle can pass through the inspection zone II as in FIG. 7 with the centering ring 28 holding it before it passes through inspection zone I where it is only held by rotatable centering ring 28.

The optoelectronic inspection system is a known type. In FIG. 5, the devices for inspecting in zone I comprise a camera 32 which projects a light beam through the bottle to a reflector 34. The reflector returns the beam to the camera 32 which beam is modulated by any light absorbing contaminant which may be present on the wall of the bottle. The difference in intensity of the reflected beam relative to a reference is indicative of the presence of a contaminant. By suitable photoelectronic devices, not shown, intensity variations are converted to corresponding electric signals which are used to bring about ejection of any bottle that contains a contaminant. As is evident in FIG. 5, most but not all of the bottle height is inspected in zone I.

Inspection zone II in FIG. 7 has similar components. Here camera 33 projects the inspection light beam through the neck and mouth region of the bottle with some overlap of the region that was previously inspected. The light beam which would be modulated by any contaminant is reflected back to camera 33 by reflector 35 and the intensity level is converted to a corresponding electric signal in a well known manner and, if the signal differs from a reference, it causes ejection of the bottle.

Figure 8:
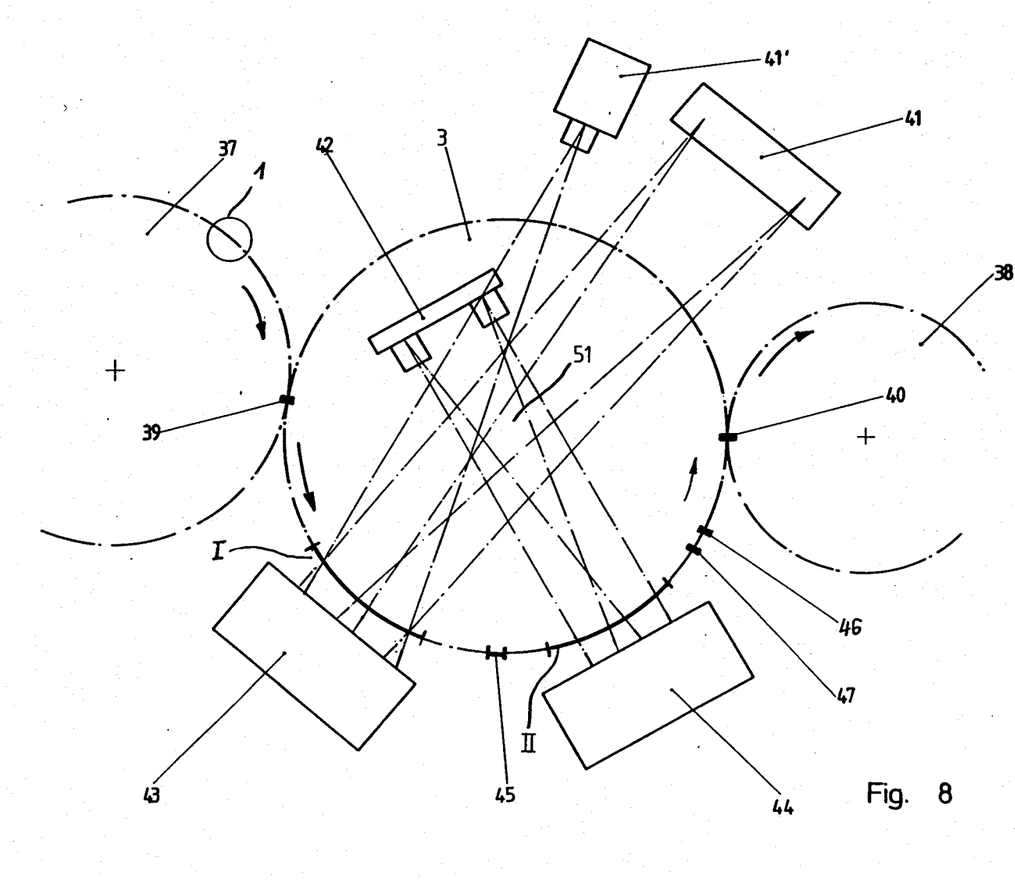
FIG. 8 is a schematic representation of the events taking place during the entire inspection process.

The FIG. 8 diagram is useful for explaining the temporal and spatial relationships that occur between the bottle infeed and outlet regions of the inspecting machine. Sensing elements detect operation of the centering members and the optoelectronic inspection elements which are cooperating with them so that an operational sequence which is interference free is achieved. The FIG. 8 diagram elaborates the optoelectronic system which is highly simplified in FIGS. 5 and 7.

In FIG. 8, the table 3 is rotating in the direction of the arrows adjacent an infeed star wheel 37 that feeds bottles 1 to the rotating disks 2 on bottle table 3. The disks are not shown in FIG. 8. There is outlet star wheel 38 also adjacent rotating table 3 for taking the bottles away after they are inspected. The bottle infeed transfer point is marked 39 and the bottle outlet transfer point is marked 40. To assure that the central shaft 51 of the bottle table 3 does not cause an obstruction in the optoelectronic operation between the camera 41', dual camera 41, 42 and the bottle wall illuminator 43 and 44 the region of radiation for the cameras 41 and 42 are guided past the center support on both sides. The centering socket 4 is placed on the bottle at the transfer point 39 by the action of cam 8 on follower 7 and the bottle is gripped by centering socket 4 as it passes through inspection zone I and beyond at the end of the bottle wall illumination device 43. When in inspection zone I, most of the body of the bottle is inspected as illustrated in FIG. 5. During this time the centering ring 28 is not engaged with the bottle but is located above it as shown in FIG. 5. Since gripping of the bottles by one device or the other must not be interrupted while they are on the rotation table 3, each bottle in the region 45 in FIG. 8 is held for a short rotation time simultaneously by centering socket 4 and centering ring 28 as illustrated in FIG. 6. While the centering socket 4 is subsequently raised upward over the region of vessel head illumination device 44, the centering ring 28 remains in the applied position in inspection zone II until the centering socket 4 again grasps the bottle prior to the discharge position 40 in order to assure the interference free transfer to the outlet star 38. The point where the centering socket 4 grips the bottle again is marked 47. At the point marked 46, the centering ring 28 is driven upward by the action of cam 14 on follower roller 13. The centering socket 4 is not released from the bottle mouth until the bottle is at transfer point 40 where it is engaged by the outlet star wheel 38. Both centering elements remain in upwardly retracted or resting position at least until the transfer point 39 for new vessels is reached after which the centering socket 4 is operated to grasp a bottle delivered from the feed star 37.

We claim:

1. A method of inspecting bottles for foreign bodies and other contaminants by passing said bottles through consecutive optoelectronic inspection zones in either order, comprising:
    gripping the bottle at its mouth while the bottom of the bottle is on a support to provide an unobstructed view of the bottle wall from the bottom to near the mouth of the bottle while the bottle is passing through and is being scanned in one of said optoelectronic inspection zones, and
    gripping the bottle at about its shoulder while the bottom of the bottle is on said support to provide an unobstructed view of the shoulder and neck region from where it is gripped up to the mouth of the bottle while the bottle is passing through and is being scanned in the other of said optoelectronic inspection zones.

2. The method according to claim 1 wherein each bottle is rotated about its axis during scanning in each of the inspection zones.

3. A method of inspecting bottles for foreign bodies and other contaminants by passing said bottles through consecutive optoelectronic inspection zones in either order, comprising:
    gripping the bottle at is mouth while the bottom of the bottle is on a support to provide an unobstructed view of the bottle wall from the bottom to near the mouth of the bottle while the bottle is passing through and is being scanned in one of said optoelectronic inspection zones, and
    gripping the bottle at about its shoulder while the bottom of the bottle is on said support to provide an unobstructed view of the shoulder and neck region from where it is gripped up to the mouth of the bottle while the bottle is passing through and is being scanned in the other of said optoelectronic inspection zones,
    each bottle being gripped at its mouth and at its shoulder region simultaneously while on said support in the zone between inspection zones and one of the grips is released and the other of the grips is maintained before the bottle enters the next inspection zone.

4. A method of inspecting bottles for foreign bodies and other contaminants by passing said bottles through consecutive optoelectronic inspection zones in either order, comprising:
    gripping the bottle at its mouth while the bottom of the bottle is on a support and rotating therewith to provide an unobstructed view of the bottle wall from the bottom to near the mouth of the bottle while the bottle is passing through and is being scanned in one of said optoelectronic inspection zones, and
    gripping the bottle at about its shoulder while the bottom of the bottle is on said support and rotating therewith to provide an unobstructed view of the shoulder and neck region from where it is gripped up to the mouth of the bottle while the bottle is passing through and is being scanned in the other of said optoelectronic inspection zones,
    at least part of the neck region and the body of the bottle being scanned in the first inspection zone and in the second or next successive inspection zone through which said bottle passes the top region and part of the neck region of said bottle is scanned,
    each bottle being gripped at its mouth and at its shoulder region simultaneously while on said support in the zone between inspection zones and one of the grips is released and the other of the grips is maintained before the bottle enters the next inspection zone.

5. Apparatus for inspecting bottles for foreign bodies and other contaminants, comprising:
- at least two successive bottle inspection zones and electronic devices in said zones for optically scanning said bottles to determine the presence or absence of said foreign bodies and contaminants in said bottles,
- a plurality of disk means and means for translating said disk means through said inspection zones with bottles standing upright on said disk means,
- movable support means arranged above each disk means for translating correspondingly with said disk means,
- a centering socket member mounted on said support means for being lowered to grip the mouth of a bottle on a disk means and for being raised clear of said bottle,
- driving means for driving said centering socket member down and up,
- a centering ring member mounted n said support means for being lowered to grip said bottle in the shoulder region and for being raised clear of said bottle,
- driving means for driving said centering ring member down and up,
- said driving means operating in a timing relationship with each other that results in said centering socket member gripping said bottle at its mouth while said bottle is moving through one of said inspection zones and that results in said ring member gripping said bottle at its shoulder region while said bottle is moving through the other inspection zone,
- said timing relationship being such that the centering socket member and the centering ring member are both lowered to grip the bottle at the mouth and at the shoulder region when the bottle is in a transition zone between inspection zones and one member is raised to clear the bottle in the transition zone.

6. The apparatus according to claim 5 wherein said centering ring member is mounted to said support means by means including at least one rod means mounted for moving vertically in said support means, said centering ring member being fastened to said rod means,
- said rod means being parallel to the axis of the bottle on said disk such that when viewed in the direction of translation of the bottle said rod means resides in front of the bottle or behind the bottle so a light beam can pass unhindered through the top region of the bottle transversely to the direction of translation of the bottles when said bottle is in an inspection zone and is being grasped by said centering ring member.

7. The apparatus according to any one of claims 5 or 6 wherein the inside diameter of the centering ring member is greater than the outside dimension of said centering socket member.

8. The apparatus according to any one of claims 5 or 6 wherein said centering ring member comprises a body, bearing means in the body and a ring of resilient material, by which said bottle is gripped, rotatable on said bearing means.

9. The apparatus according to claim 5 including:
- a rotary table on which said disk means are arranged in a circle and are mounted for rotation about axes parallel to the rotational axis of the table,
- a bottle infeed star wheel adjacent said table and a bottle outlet star wheel adjacent said table circumferentially displaced from said infeed star wheel,
- said driving means responding to a bottle on a disk means in the region where said bottle has been transferred from said infeed star wheel and responding to a bottle on a disk means in the region where said bottle is transferred to said outlet star wheel by in both cases driving said centering socket member down to grip said bottle and driving said centering ring member up clear of said bottle.

10. The apparatus according to claim 5 wherein when said bottle is gripped at its mouth in one of the inspection zones the entire wall of the body of the bottle and part of the neck are scanned and inspected and when said bottle is gripped at its shoulder region in the other inspection zone the height of the neck and head of the bottle are scanned and inspected.

* * * * *